US009341639B2

(12) United States Patent
Chien et al.

(10) Patent No.: US 9,341,639 B2
(45) Date of Patent: May 17, 2016

(54) APPARATUS FOR MICROFLUID DETECTION

(71) Applicant: Industrial Technology Research Institute, Hsinchu (TW)

(72) Inventors: Liang-Ju Chien, Kaohsiung (TW); Chi-Han Chiou, Tainan (TW); Shao-Hsing Yeh, Hsinchu (TW); Yu-Ying Lin, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 8 days.

(21) Appl. No.: 14/221,286

(22) Filed: Mar. 21, 2014

(65) Prior Publication Data
US 2015/0029491 A1    Jan. 29, 2015

(30) Foreign Application Priority Data

Jul. 26, 2013 (TW) .............................. 102126955 A
Sep. 6, 2013 (TW) .............................. 102132268 A

(51) Int. Cl.
*G01N 35/00* (2006.01)
*B01L 3/00* (2006.01)

(52) U.S. Cl.
CPC ...... *G01N 35/0098* (2013.01); *B01L 3/502792* (2013.01); *B01L 2200/0668* (2013.01); *B01L 2300/087* (2013.01); *B01L 2300/1861* (2013.01); *B01L 2400/043* (2013.01)

(58) Field of Classification Search
CPC .............................. G01N 1/28; G01N 35/0098
See application file for complete search history.

(56) References Cited

U.S. PATENT DOCUMENTS

| 6,152,181 | A  | 11/2000 | Wapner et al. |
| 7,544,955 | B2 | 6/2009  | Boutet |
| 7,820,454 | B2 | 10/2010 | Su et al. |
| 8,088,578 | B2 | 1/2012  | Hua et al. |
| 8,137,917 | B2 | 3/2012  | Pollack et al. |

(Continued)

FOREIGN PATENT DOCUMENTS

| CA | 2476953 | 6/2012 |
| CN | 101375166 | 2/2009 |

(Continued)

OTHER PUBLICATIONS

Asakura et al., "Deformation and motion by gravity and magnetic field of a droplet of water-based magnetic fluid on a hydrophobic surface," Applied Surface Science, Aug. 2006, pp. 3098-3102.

(Continued)

*Primary Examiner* — Tarifur Chowdhury
*Assistant Examiner* — Omar Nixon
(74) *Attorney, Agent, or Firm* — Jiang Chyun IP Office

(57) ABSTRACT

A apparatus for microfluid detection for detecting a sample fluid including a plurality of magnetic particles is provided. The apparatus for microfluid detection includes a microfluidic chip and a magnetic generating module. The microfluidic chip includes a substrate and microfluidic channels, wherein the sample fluid is carried by a carry surface of the substrate. The magnetic generating module is adapted for providing a positioning magnetic field and a surrounding magnetic field. The magnetic module controls to move the sample fluid and change a distribution of the magnetic particles in the sample fluid through the positioning magnetic field and the surrounding magnetic field.

17 Claims, 9 Drawing Sheets

(56) References Cited

U.S. PATENT DOCUMENTS

| | | | |
|---|---|---|---|
| 8,208,146 | B2 | 6/2012 | Srinivasan et al. |
| 8,344,731 | B2 | 1/2013 | Lee |
| 2003/0210287 | A1 | 11/2003 | Harding et al. |
| 2004/0077105 | A1 | 4/2004 | Wu et al. |
| 2007/0238112 | A1* | 10/2007 | Sohn et al. .......... 435/6 |
| 2008/0160622 | A1* | 7/2008 | Su et al. .......... 436/86 |
| 2008/0166793 | A1 | 7/2008 | Beer et al. |
| 2009/0318786 | A1 | 12/2009 | Blank et al. |
| 2010/0068764 | A1 | 3/2010 | Sista et al. |
| 2010/0233822 | A1* | 9/2010 | Prins et al. .......... 436/164 |
| 2011/0003325 | A1 | 1/2011 | Durack |
| 2011/0275985 | A1 | 11/2011 | Lowery, Jr. et al. |
| 2013/0016335 | A1* | 1/2013 | Lo et al. .......... 356/28 |

FOREIGN PATENT DOCUMENTS

| | | |
|---|---|---|
| CN | 101460837 | 3/2012 |
| CN | 102625850 | 8/2012 |
| CN | 102719357 | 10/2012 |
| DE | 3855814 | 10/1997 |
| DE | 19782096 | 3/2000 |
| EP | 0563251 | 10/1993 |
| EP | 0563271 | 10/1993 |
| EP | 0820523 | 1/1998 |
| EP | 0910578 | 4/1999 |
| EP | 0931259 | 7/1999 |
| EP | 0937096 | 8/1999 |
| EP | 0959985 | 12/1999 |
| EP | 1087985 | 4/2001 |
| EP | 1341655 | 9/2003 |
| EP | 1412729 | 4/2004 |
| EP | 2396654 | 12/2011 |
| GB | 1111511 | 5/1968 |
| JP | 2005537852 | 12/2005 |
| JP | 2007513650 | 5/2007 |
| JP | 4412874 | 2/2010 |
| KR | 20080110575 | 12/2008 |
| RU | 2008152757 | 7/2010 |
| TW | I246942 | 1/2006 |
| TW | I306153 | 2/2009 |
| TW | 200912310 | 3/2009 |
| TW | I381414 | 1/2013 |
| WO | 8905977 | 6/1989 |
| WO | 9924065 | 5/1999 |
| WO | 03089709 | 10/2003 |
| WO | 2007073258 | 6/2007 |
| WO | 2009052123 | 4/2009 |
| WO | 2009113010 | 9/2009 |

OTHER PUBLICATIONS

Afkhami et al., "Deformation of a hydrophobic ferrofluid droplet suspended in a viscous medium under uniform magnetic fields," Journal of Fluid Mechanics, Nov. 2010, pp. 358-384.

Afkhami, "Motion and deformation of a hydrophobic ferrofluid droplet in a viscous medium under non-uniform magnetic fields," DFD09 Meeting of the American Physical Society, Sep. 9, 2009, pp. 1.

Zhong et al., "Multiplex digital PCR: breaking the one target per color barrier of quantitative PCR," Lab Chip, Jul. 2011, pp. 2167-2174.

Lehmann et al., "Two-dimensional magnetic manipulation of microdroplets on a chip as a platform for bioanalytical applications," Sensors and Actuators B: Chemical, Oct. 12, 2006, pp. 457-463.

Iino et al., "Femtoliter Microdroplet Array Device for Single-Molecule Digital Enzyme-Linked Immunosorbent Assay," 15th International Conference on Miniaturized Systems for Chemistry and Life Sciences, Oct. 2-6, 2011, pp. 24-26.

Lehmann et al., "On-chip antibody handling and colorimetric detection in a magnetic droplet manipulation system," Microelectronic Engineering, May-Aug. 2007, pp. 1669-1672.

Su et al., "Defect-Oriented Testing and Diagnosis of Digital Microfluidics-Based Biochips," Proceedings of IEEE International Test Conference, 2005, Nov. 8, 2005, pp. 1-10.

"Office Action of Taiwan Counterpart Application", issued on Mar. 13, 2015, p. 1-p. 7.

"Office Action of China Counterpart Application", issued on Oct. 29, 2015, p. 1-p. 6.

* cited by examiner

APPARATUS FOR MICROFLUID DETECTION

CROSS-REFERENCE TO RELATED APPLICATION

This application claims the priority benefit of Taiwan application serial no. 102126955, filed on Jul. 26, 2013, and Taiwan application serial no. 102132268, filed on Sep. 6, 2013. The entirety of each of the above-mentioned patent applications is hereby incorporated by reference herein and made a part of this specification.

BACKGROUND

1. Technical Field

The disclosure relates to an apparatus for microfluid detection.

2. Related Art

To satisfy demands of emphasis on preventive medicine, early diagnosis and early treatment in medical treatment, demands on test environment automation, point of care (POC) or near patient testing and molecular diagnosis are increased. According to an ideal molecular diagnosis system criterion provided by WHO (World Health Organization), in a global molecular diagnosis market report of 2009, estimated sales values of the global molecular diagnosis market from 2015 to 2019 are respectively 15.5 billion and 42.5 billion U.S. dollars, and average annual growth rates are respectively 11.5% and 22.4%. Currently, there are thousands of biomarkers and biomarker candidates that have been published in journals and patents, which are increased by one hundred types annually. Therefore, a future development trend of healthcare will be more dependent on personalized molecular medicine testing database for providing personalized healthcare, for example, screening for drug safety and drug efficacy track, etc.

In application of POC, since a microfluid technique has characteristics of less required samples, small volume of a testing chip and low energy consumption, it is commonly used in an in-vitro testing market, which is generally used in collaboration with an optical testing device to implement sample testing of a large amount. Although many different method have been developed for the current microfluid testing, since a sample droplet has a tiny volume, and it is not easy to control a position thereof, regarding the optical testing requiring accurate positioning, it is still difficult in positioning, especially, a height of the droplet, a light transmission path and interference of particles in the droplet may directly influence a result of the optical testing. However, regarding disease or drug testing, a reliable testing method is very important for the testing result. Therefore, how to effectively control positions of the sample droplet on the testing chip and microfluidic channels and decrease the interference of the particles in the droplet on the optical testing has become one of the problems to be resolved.

SUMMARY

The disclosure is directed to an apparatus for microfluid detection, which is adapted to detect a sample fluid including a plurality of magnetic particles. The apparatus for microfluid detection includes a microfluidic chip and a magnetic generating module. The microfluidic chip includes a substrate and microfluidic channels formed on the substrate, wherein the sample fluid is carried by a carry surface of the substrate. The magnetic generating module includes a ring-shape hollow magnetic generating module and a surrounding magnetic generating module, where the ring-shape hollow magnetic generating module is disposed on at least one side of the carry surface, and the ring-shape hollow magnetic generating module is adapted to provide a positioning magnetic field to the sample fluid. The surrounding magnetic generating module is disposed at periphery of the microfluidic chip, and the surrounding magnetic generating module is adapted to provide a surrounding magnetic field to the sample fluid. The magnetic generating module controls to move the sample fluid and change a distribution of the magnetic particles in the sample fluid through the positioning magnetic field and the surrounding magnetic field.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

Figure 1A:
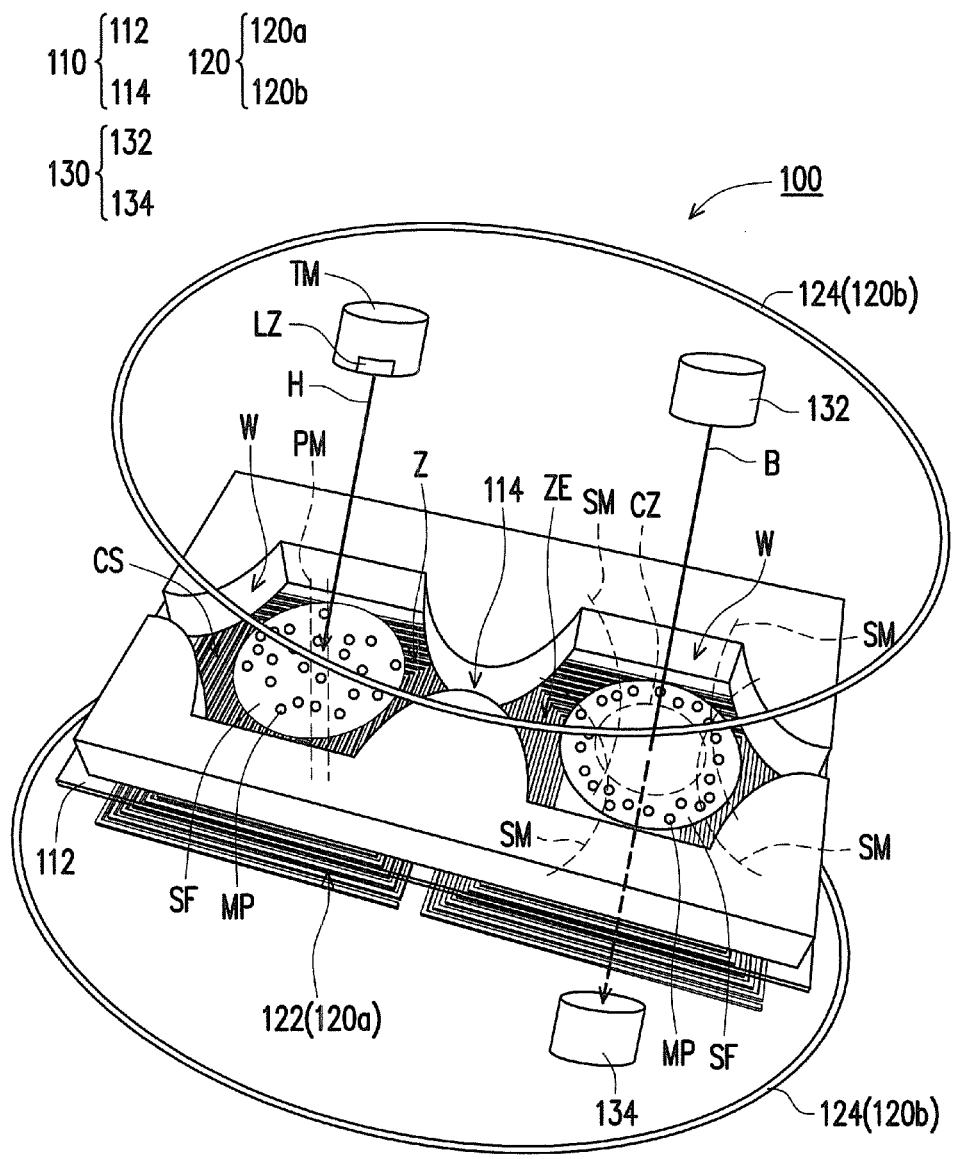
FIG. 1A is a side view of an apparatus for microfluid detection according to an embodiment of the disclosure.

FIG. 1A is a side view of an apparatus for microfluid detection according to an embodiment of the disclosure. Referring to FIG. 1A, in the present embodiment, the apparatus for microfluid detection 100 is adapted to detect a sample fluid (SF) including a plurality of magnetic particles (MP). The apparatus for microfluid detection 100 includes a microfluidic chip 110 and a magnetic generating module 120. The microfluidic chip 110 includes a substrate 112 and microfluidic channels 114 formed on the substrate 112, wherein the sample fluid SF is carried by a carry surface CS of the substrate 112. The magnetic generating module 120 includes a ring-shape hollow magnetic generating module 120a and a surrounding magnetic generating module 120b, where the ring-shape hollow magnetic generating module 120a is disposed on at least one side of the carry surface CS, and the ring-shape hollow magnetic generating module 120a is adapted to provide a positioning magnetic field PM to the sample fluid SF. The surrounding magnetic generating module 120b is disposed at periphery of the microfluidic chip 110, and the surrounding magnetic generating module 120b is adapted to provide a surrounding magnetic field (SM) to the sample fluid SF. The magnetic generating module 120 controls the sample fluid SF and changes a distribution of the magnetic particles MP in the sample fluid SF through the positioning magnetic field PM and the surrounding magnetic field SM.

Moreover, in the present embodiment, in order to implement optical detection, the apparatus for microfluid detection 100 further includes an optical detection module 130. The optical detection module 130 can be disposed on at least one side of the carry surface CS and includes a light source 132 and a detector 134. The light source 132 provides a detection beam B to the sample fluid SF. The ring-shape hollow magnetic generating module 120a and the surrounding magnetic generating module 120b may drive the magnetic particles MP to spread, so as to form a central zone (CZ) without the magnetic particles (MP) in the sample fluid SF, and the detection beam B may passes through the central zone (CZ) and is transmitted to the detector 134. More details will be further described in the following paragraphs.

In the present embodiment, the light source 132 of the optical detection module 130 can be disposed at a side different to that of the ring-shape hollow magnetic generating module 120a relative to the microfluidic chip 110, and the detector 134 can be disposed at a side the same to that of the ring-shape hollow magnetic generating module 120a relative to the microfluidic chip 110, as that shown in FIG. 1A. The microfluidic chip 110 of the present embodiment is light transparent, and a detection beam B can be transmitted to the detector 134 through the sample fluid SF and the microfluidic chip 110. However, in different embodiments, the optical detection module may have different implementations according to different designs of optical path, for example, if the microfluidic chip is a light reflective mirror, the optical detection module 130 can be only disposed on the upper side or the lower side of the carry surface CS, i.e. the light source 132 and the detector 134 can be disposed at the same side of the microfluidic chip 110 and located at the same side with that of the carry surface CS, and the detection beam B may pass through the sample fluid SF, and is reflected by the microfluidic chip 110, and is then transmitted to the detector 134, which is not limited by the disclosure.

In detail, in the present embodiment, a material of the substrate 112 can be a transparent material such as glass, quartz or plastic, etc., which is not limited by the disclosure. The magnetic particles MP is blended with the sample fluid SF in advance, or is disposed on the microfluidic chip 110 for directly blending with the sample fluid SF after the sample fluid SF is dropped on the microfluidic chip 110. Moreover, in the present embodiment, the magnetic particles MP are, for example, a paramagnetic material particles, though the disclosure is not limited thereto.

Moreover, in the present embodiment, besides the sample fluid SF (aqueous solution), the carry surface CS in the apparatus for microfluid detection 100 also carries an oily solution, which is used for preventing evapotranspiration of the sample fluid SF during operation, and another effect is that the aqueous solution has surface tension in the environment of the oily solution to form a droplet to facilitate the detection, though the disclosure is not limited thereto.

In detail, referring to FIG. 1A, in the present embodiment, during the operation, the sample fluid SF can be dropped in an operational zone Z on the substrate 112 to perform pre-test procedures such as blending and heating, etc. Then, the ring-shape hollow magnetic generating module 120a provides the positioning magnetic field PM to the sample fluid SF, and the positioning magnetic field PM may drive the sample fluid SF to move from the operational zone Z of the substrate 112 to a desired position at a zone for examination ZE on the substrate 112 through the microfluidic channels 114, so as to be ready for subsequent testing.

In other words, by generating the positioning magnetic field PM, the ring-shape hollow magnetic generating module 120a can move and position the sample fluid SF through a manner of attracting or repelling the magnetic particles MP. Therefore, the position of the sample fluid SF on the microfluidic chip 110 can be accurately controlled, so as to accurately implement the subsequent optical testing. Moreover, the sample fluid SF can be moved without contact and guide of other matters, so as to avoid contaminating the sample fluid SF.

Meanwhile, in the present embodiment, if the magnetic particles MP are configured on the operational zone Z, when the sample liquid SF is dropped on the operational zone Z to contact the magnetic particles MP, the ring-shape hollow magnetic generating module 120a can also exert a more even magnetic field to the sample fluid SF to evenly blend the magnetic particles MP and the sample fluid SF, which avails subsequently moving the sample fluid SF, so as to avoid uneven distribution of the magnetic particles MP in the sample fluid SF that probably causes a situation that a part of the sample fluid carrying more magnetic particles MP is separated from the sample fluid SF when the sample fluid SF is moved.

Figure 2A:
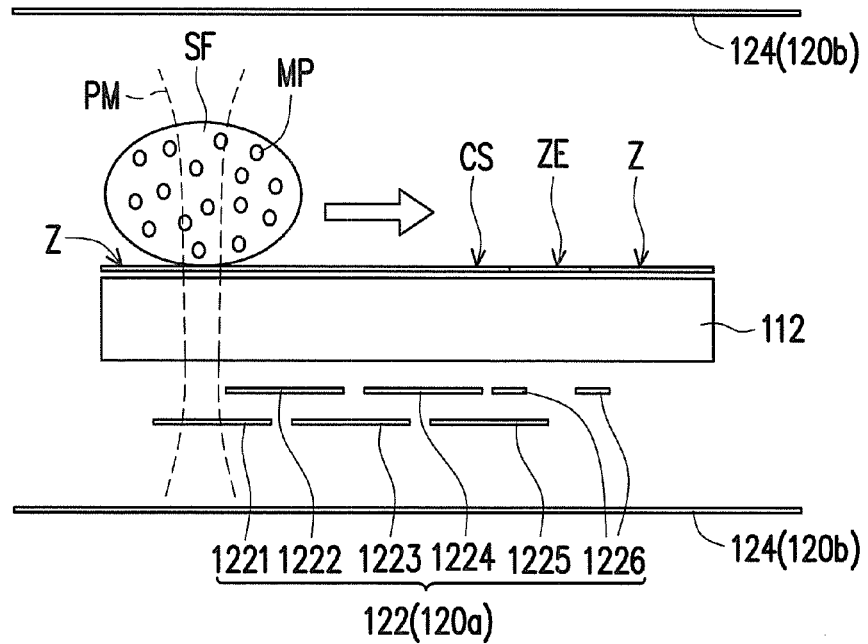
FIG. 2A to FIG. 2D are side views of the apparatus for microfluid detection in the embodiment of FIG. 1A.
Figure 2B:
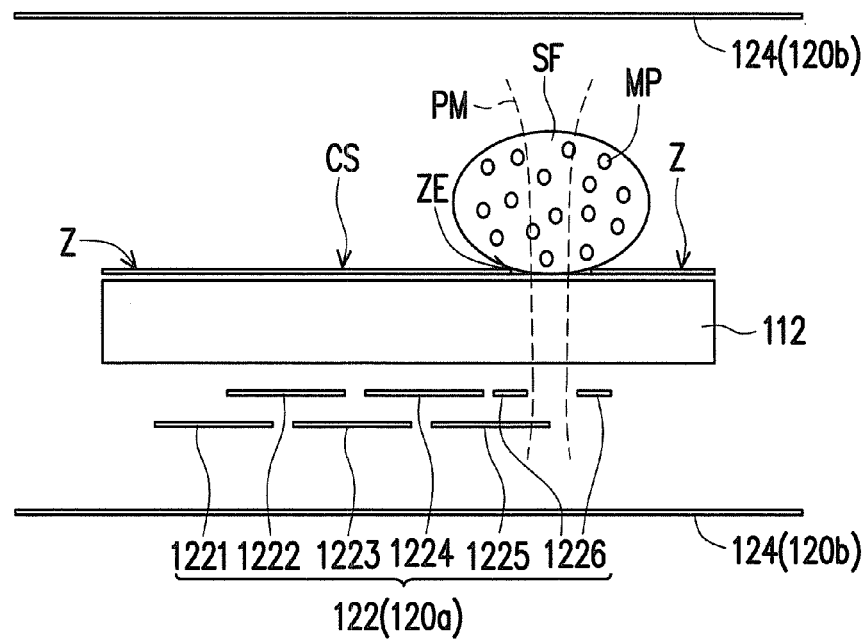
Figure 2C:
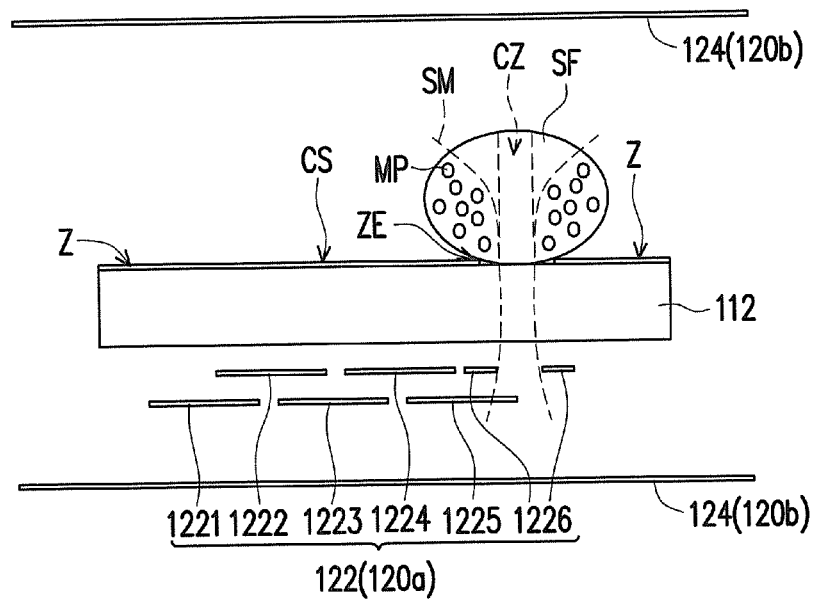

On the other hand, referring to FIG. 1A, in the present embodiment, when the sample fluid SF is moved to the zone for examination ZE for examination, a current inverted to that of the surrounding magnetic generating module 120b is inlet to a ring-shape hollow coil 1226 (referring to FIG. 2A) disposed under the zone for examination ZE in the ring-shape hollow magnetic generating module 120a, so as to drive the magnetic particles MP in the sample fluid SF to spread to the periphery of the sample liquid SF (referring to FIG. 2C). In this way, during the examination, the light source 132 of the optical detection module 130 provide a detection beam B to the sample fluid SF, and the ring-shape hollow coil 1226 disposed under the zone for examination ZE and the surrounding magnetic generating coils 124 may drive the magnetic particles MP to spread, so as to form a central zone (CZ) without the magnetic particles in the sample fluid SF, where the detection beam B may pass through the central zone CZ and is transmitted to the detector 134. The size of the sample fluid SF and the central zone CZ illustrated in FIG. 1A, and distribution status of the surrounding magnetic field SM, the positioning magnetic field PM and the magnetic particles MP only serve as a reference, and the disclosure is not limited thereto.

Therefore, the detection beam B can be transmitted into the sample fluid SF to obtain information of the sample fluid SF (for example, a fluorescence spectrum signal, a Raman spectrum signal, etc.) without irradiating the magnetic particles MP, so that a noise influence caused by the magnetic particles MP can be reduced to the minimum. Therefore, not only the position of the sample fluid SF can be accurately controlled, accuracy of the optical detection is also effectively improved.

However, in other embodiments, the information may be carried by the magnetic particles MP or the information may be amplified by the magnetic particles MP. Therefore, in that case, it may achieve stronger signals when directing the detection beam B to the magnetic particles MP. FIG. 2E is another side view of the apparatus for microfluid detection in another embodiment when the magnetic particles are concentrated. Referring to FIG. 2E, the ring-shape hollow coil 1226 disposed under the zone for examination ZE and the surrounding magnetic generating coils 124 may drive the magnetic particles MP to gather in the sample fluid SF, such that the magnetic particles may be concentrated in the central zone CZ of the sample fluid SF, where the detection beam B may pass through the central zone CZ and is transmitted to the detector 134.

In this way, the detection beam B can be transmitted into the sample fluid SF to obtain information of the sample fluid SF and of the magnetic particles MP (for example, a fluorescence spectrum signal, a Raman spectrum signal, etc.) when irradiating the magnetic particles MP, so that a stronger signal of the information carried by the magnetic particles MP may be obtained. Therefore, not only the position of the sample fluid SF can be accurately controlled, accuracy of the optical detection is also effectively improved.

In detail, in the present embodiment, the light source 132 can be a laser, a light-emitting diode (LED), a halogen lamp, a mercury lamp, etc. The detector 134 can be a complementary metal-oxide semiconductor (CMOS) sensor, a charge coupled device (CCD) sensor, a spectrometer, a photodiode, a photomultiplier tube, etc., which is not limited by the disclosure.

Moreover, referring back to FIG. 1A, in the present embodiment, the apparatus for microfluid detection 100 further includes a thermal-modulation module TM, which is disposed on at least one side of the carry surface CS, and the thermal-modulation module TM selectively increases or decreases a temperature of the sample fluid SF. The thermal-modulation module TM may include various heating or cooling devices such as a heating module, a thermal electric cooling module, etc., which is not limited by the disclosure. For example, in the present embodiment, the thermal-modulation module TM may include a laser heater LZ, and the laser heater LZ may provide a heating beam H to the sample fluid SF for heating. In this way, when the apparatus for microfluid detection 100, for example, detects a DNA sequence, the apparatus for microfluid detection 100 may first heat the sample in the operational zone Z to separate a single strand of the DNA, and then move the sample to the adjacent zone for examination ZE for examination, so as to improve the efficiency of the whole detection and decrease an error of the detection. It should be noticed that in the present embodiment, configuration positions of the thermal-modulation module TM and the laser heater LZ are only used for schematically describing the present embodiment, which may have other implementations in other embodiments, and is not limited by the disclosure.

Figure 1B:
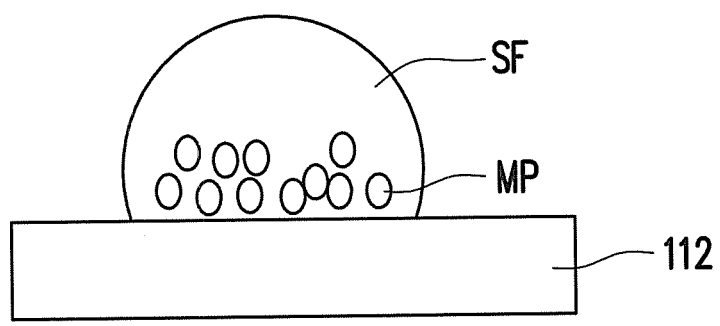
FIG. 1B to FIG. 1D are schematic diagrams illustrating another implementation of the embodiment of FIG. 1A.
Figure 1C:
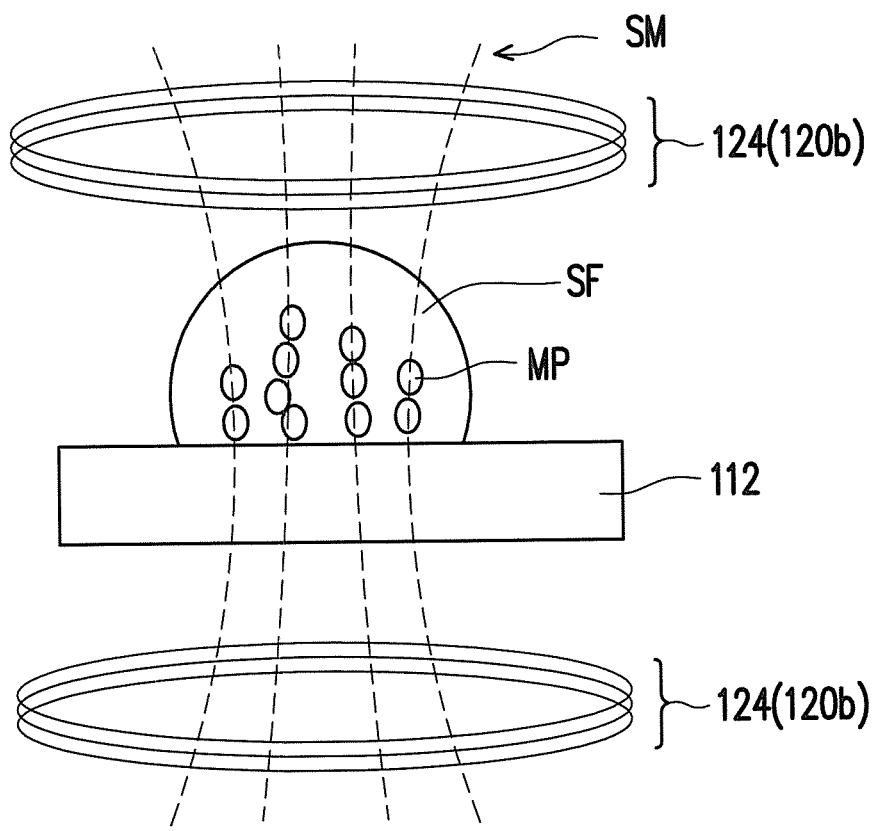
Figure 1D:
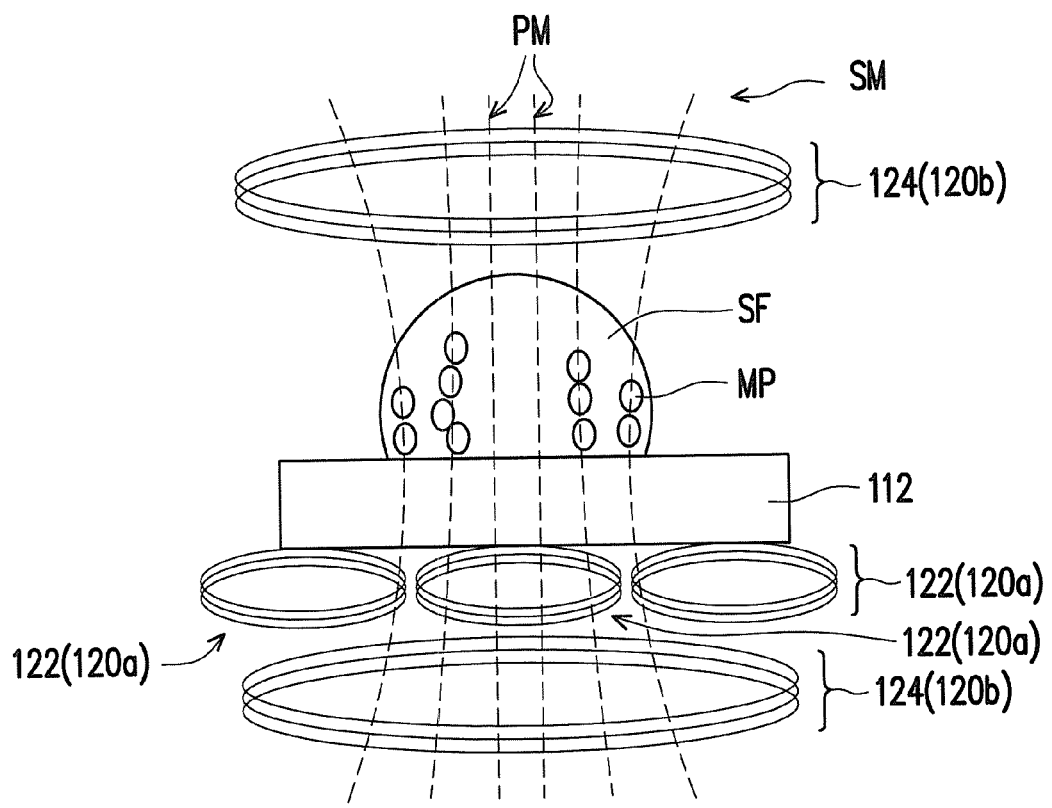

Moreover, FIG. 1B to FIG. 1D are schematic diagrams illustrating another implementation of the embodiment of FIG. 1A. Referring to FIG. 1B to FIG. 1D, where FIG. 1B illustrates a situation that the sample fluid SF is disposed on the substrate 112 without a magnetic field around, and now the magnetic particles MP are distributed at a lower part of the sample fluid SF that is closer to the substrate 112 due to gravity.

When the sample fluid SF is disposed on the substrate 112, and the surrounding magnetic generating module 120b provides the surrounding magnetic field SM, the magnetic particles MP are influenced by the surrounding magnetic field SM provided by the surrounding magnetic generating module 120b, and the magnetic particles MP in the sample fluid SF form a plurality of columnar stacking patterns in the sample fluid SF (shown in FIG. 1C).

Further, when the surrounding magnetic generating module 120b provides the surrounding magnetic field SM, and a positioning magnetic generating coils 122 provides the positioning magnetic field PM with polarity opposite to that of the surrounding magnetic field SM, the magnetic particles MP in the sample fluid SF not only form a plurality of columnar stacking patterns in the sample fluid SF, but are also repelled to the periphery of the sample fluid SF. In this way, by adjusting a polarity relationship between the surrounding magnetic field SM and the positioning magnetic field PM, a distribution state of the magnetic particles MP in the sample fluid SF can be controlled.

FIG. 2A to FIG. 2D are side views of the apparatus for microfluid detection in the embodiment of FIG. 1A. In FIG. 2A to FIG. 2D, for simplicity's sake, components such as side walls W, etc. in the figures are omitted, referring to FIG. 1A-FIG. 2D, in the present embodiment, the ring-shape hollow magnetic generating module 120a of the magnetic generating module 120 may include a plurality of positioning magnetic generating coils 122 disposed and arranged at the upper side or lower side of the microfluidic chip 110, and the surrounding magnetic generating module 120b of the magnetic generating module 120 may include surrounding magnetic generating coils 124 disposed on at least one of the upper side and the lower side of the zone for examination ZE of the microfluidic chip 110. In the present embodiment, as that shown in FIG. 2A to FIG. 2D, the surrounding magnetic generating coils 124 are disposed on both of the upper side and the lower side of the zone for examination ZE of the microfluidic chip 110, and the positioning magnetic generating coils 122 are disposed and arranged to the lower side of the microfluidic chip 110. The positioning magnetic field PM is generated by the positioning magnetic generating coils 122, and the surrounding magnetic field SM is generated by the surrounding magnetic generating coils 124.

In detail, in the present embodiment, as that shown in FIG. 2A to FIG. 2D, the positioning magnetic generating coils 122, for example, include ring-shape coils 1221, 1222, 1223, 1224, 1225 and 1226 arranged in sequence, and when the sample fluid SF is required to be moved from the operational zone Z to the zone for examination ZE, the ring-shape coils 1221, 1222, 1223, 1224, 1225 and 1226 may sequentially provide the positioning magnetic field PM, so as to move the sample fluid SF to a desired position (for example, from a position shown in FIG. 2A to a position shown in FIG. 2B). In the present embodiment, as that shown in FIG. 2A to FIG. 2D, the ring-shape coils 1221, 1222, 1223, 1224, 1225 and 1226 are arranged in a manner of vertically piled up and partially overlapped, though such arrangement and the number of the ring-shape coils are only used as an example, and the disclosure is not limited thereto.

Figure 2D:
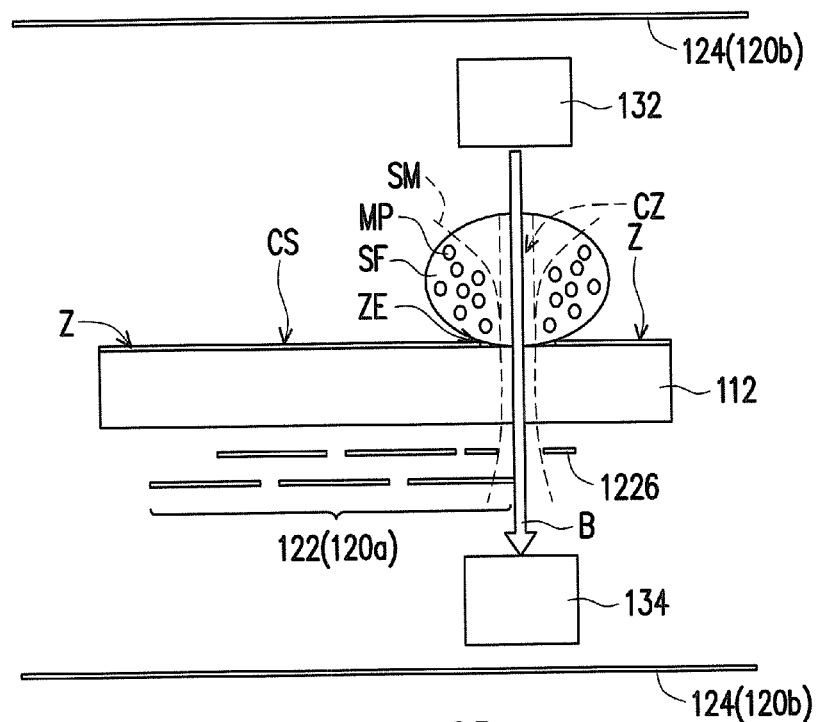
Figure 2E:
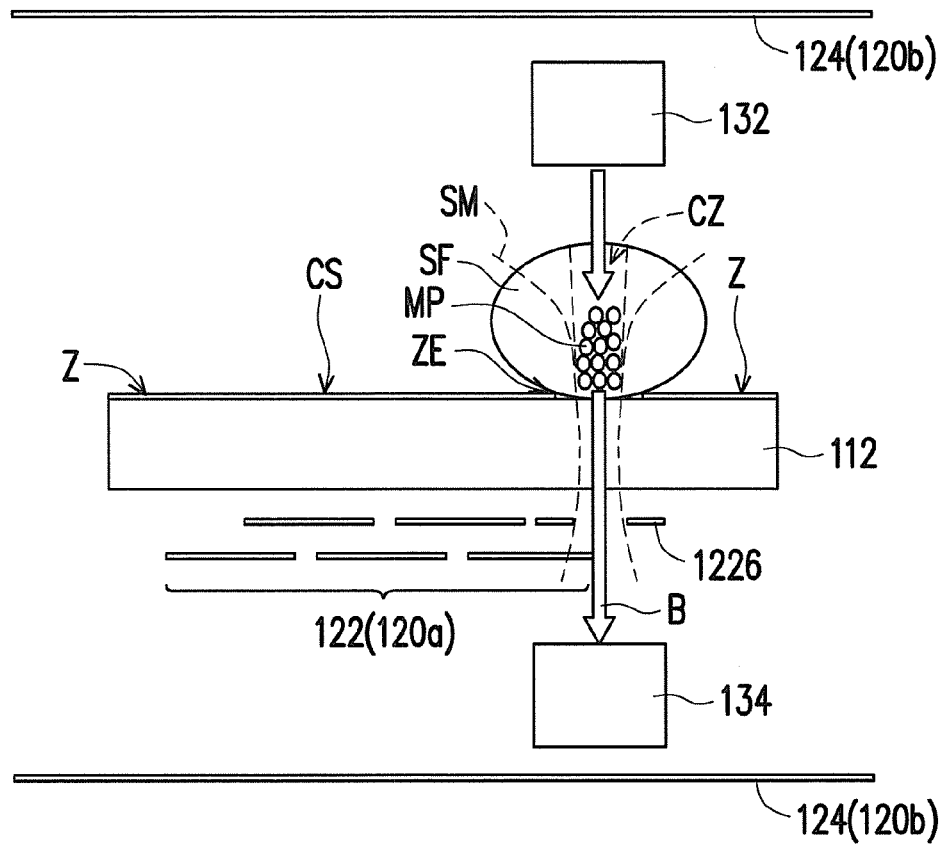
FIG. 2E is another side view of the apparatus for microfluid detection in another embodiment when the magnetic particles are concentrated.

Then, referring to FIG. 2C to FIG. 2D, in the present embodiment, after the sample fluid SF is moved to the zone for examination ZE, in order to perform the optical detection, the surrounding magnetic generating coils 124 provide the surrounding magnetic field SM so as to spread the magnetic particles MP in the sample fluid SF to form the central zone CZ that is pervious to the detection beam B, so as to reach effects of effectively controlling the position of the sample fluid SF and increasing accuracy of the optical detection.

It should be noticed that in the present embodiment, the operational zone Z may have a hydrophobicity through a hydrophobic treatment, and the zone for examination ZE may have a hydrophilicity through a hydrophilic treatment. For example, a hydrophobic layer can be coated on the surface of the microfluidic chip 110, and then the hydrophobic layer in the zone for examination ZE is removed through a plasma manner (for example, an oxygen plasma treatment) to produce the hydrophilicity. In the present embodiment, since the commonly used sample fluid SF is aqueous solution, the operational zone Z and other non-examination zones on the microfluidic chip 110 having the hydrophobicity may prevent unnecessary adhesion of the sample fluid SF. On the other hand, as the zone for examination ZE have the hydrophilicity, the sample fluid SF can be stably adhered to the zone for examination ZE after the sample fluid SF is moved to the zone for examination ZE by the positioning magnetic field PM. In this way, a strength of the positioning magnetic field PM can be decreased after the sample fluid SF is moved to the desired position, so as to effectively implement positioning and save energy.

Figure 3:
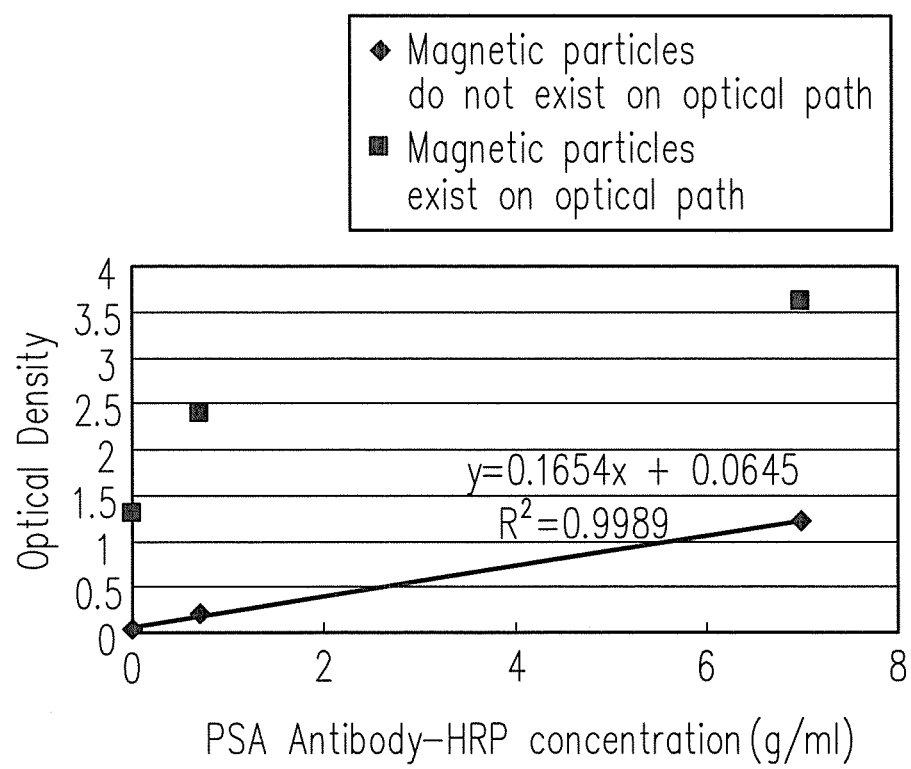
FIG. 3 is a schematic diagram of optical densities of signal measured through the apparatus for microfluid detection under situations that the surrounding magnetic generating coils function and do not function according to an embodiment of the disclosure.

FIG. 3 is a schematic diagram of optical densities of signal measured through the apparatus for microfluid detection under situations that the surrounding magnetic generating coils function and do not function according to an embodiment of the disclosure. Referring to FIG. 1 and FIG. 3, in the present embodiment, square data points represent optical densities of signal measured when the magnetic particles MP exist on the transmission path of the detection B (i.e. the surrounding magnetic generating coils 124 do not function), and diamond data points represent optical densities of signal measured when the magnetic particles MP do not exist on the transmission path of the detection B (i.e. the surrounding magnetic generating coils 124 functions). For example, when a concentration of prostate-specific antigen (PSA) antibody-horseradish peroxidase (HRP) in the sample fluid SF is increased, the optical densities of the signal measured by the optical detection module 130 is linearly increased. However, according to FIG. 3, it is obvious that when the magnetic particles MP exist on the transmission path of the detection B, the optical densities of signal measured by the optical detection module 130 are non-linearly increased. Therefore, the concentration of the PSA antibody-HRP in the sample fluid SF cannot be accurately deduced according to the measured optical densities of the signal.

However, when the surrounding magnetic generating coils 124 and the ring-shape hollow coil 1226 simultaneously function, and the magnetic particles MP are spread and do not exist on the transmission path of the detection B, the optical densities of signal measured by the optical detection module 130 are linearly increased. In other words, under the function of the surrounding magnetic generating coils 124 of the present embodiment, the influence of the magnetic particles MP on the optical signal is effectively decreased, such that the concentration of the PSA antibody-HRP can be accurately determined. It should be noticed that the compound mentioned in FIG. 3 is only used as an example, and the disclosure is not limited thereto.

Figure 4A:
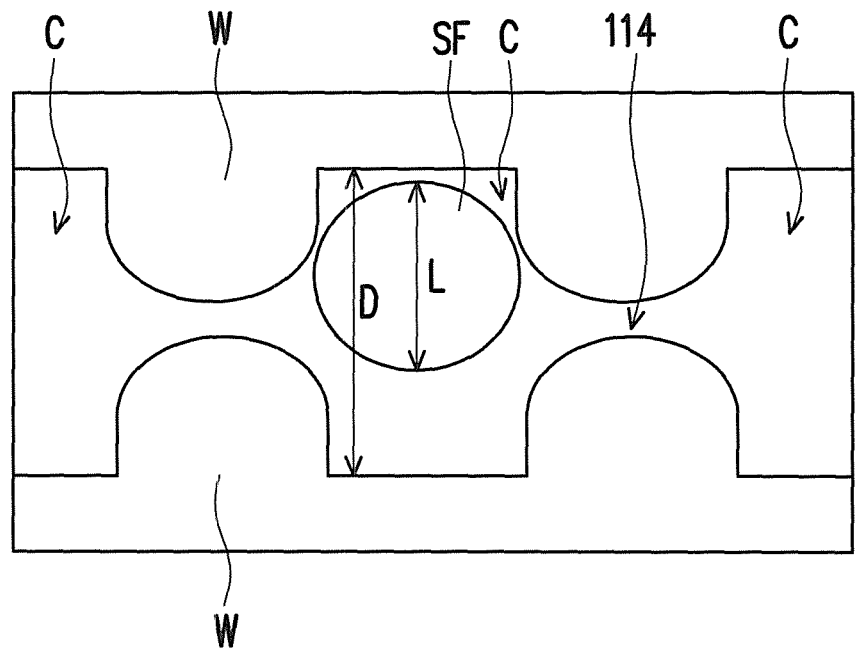
FIG. 4A is a top view of a variation of a microfluidic chip in the embodiment of FIG. 1A.
Figure 4B:
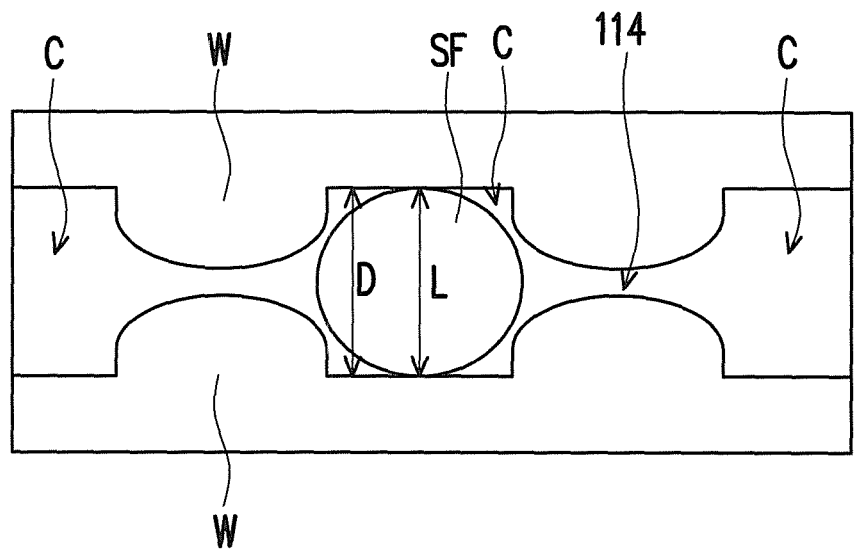
FIG. 4B is a top view of another variation of the microfluidic chip in the embodiment of FIG. 1A.

FIG. 4A is a top view of a variation of the microfluidic chip in the embodiment of FIG. 1A, and FIG. 4B is a top view of another variation of the microfluidic chip in the embodiment of FIG. 1A. Referring to FIG. 1A, FIG. 4A and FIG. 4B, in the present embodiment, the microfluidic chip 110 includes side walls W at least located to both sides of the microfluidic channels 114, the operational zone Z and the zone for examination ZE are chambers C formed by the side walls W, the microfluidic channels 114 are slits between the chambers C, and sizes of the operational zone Z and the zone for examination ZE are greater than that of the microfluidic channels 114. In this way, the sample fluid SF can move between the chambers C through the microfluidic channels 114 under control of the positioning magnetic field PM, and can be confined within the chambers C, so as to increase accuracy of positioning. It should be noticed that the shape of the chambers C shown in FIG. 4A and FIG. 4B are only an example of the embodiment, and the disclosure is not limited thereto.

Further, in the present embodiment, a distance D between the side walls W at two sides of the operational zone Z and the zone for examination ZE is approximately the same to a length L of the sample fluid SF. Therefore, after the sample fluid SF passes through the microfluidic channels 114, the sample fluid SF can be stably confined in the operational zone Z and the zone for examination ZE by the side walls W and is not easy to be shaken by external force to change the position thereof, such that the sample fluid SF can be more stably and accurately positioned in the zone for examination ZE.

Moreover, it should be noticed that the magnetic particles MP are, for example, the paramagnetic material particles, and the positioning magnetic field PM and the surrounding magnetic field SM may, for example, attract the magnetic particles MP to control the distribution of the magnetic particles MP through the aforementioned method. However, in other embodiments, the magnetic particles MP can also be diamagnetic material particles, and the positioning magnetic field PM and the surrounding magnetic field SM may, for example, repel the magnetic particles MP to achieve the same effect as that of the paramagnetic material particles through similar method, which is not limited by the disclosure. Besides, in this embodiment, the magnetic particles MP may be microparticles or nano-particles, which is not limited by the disclosure.

Figure 5:
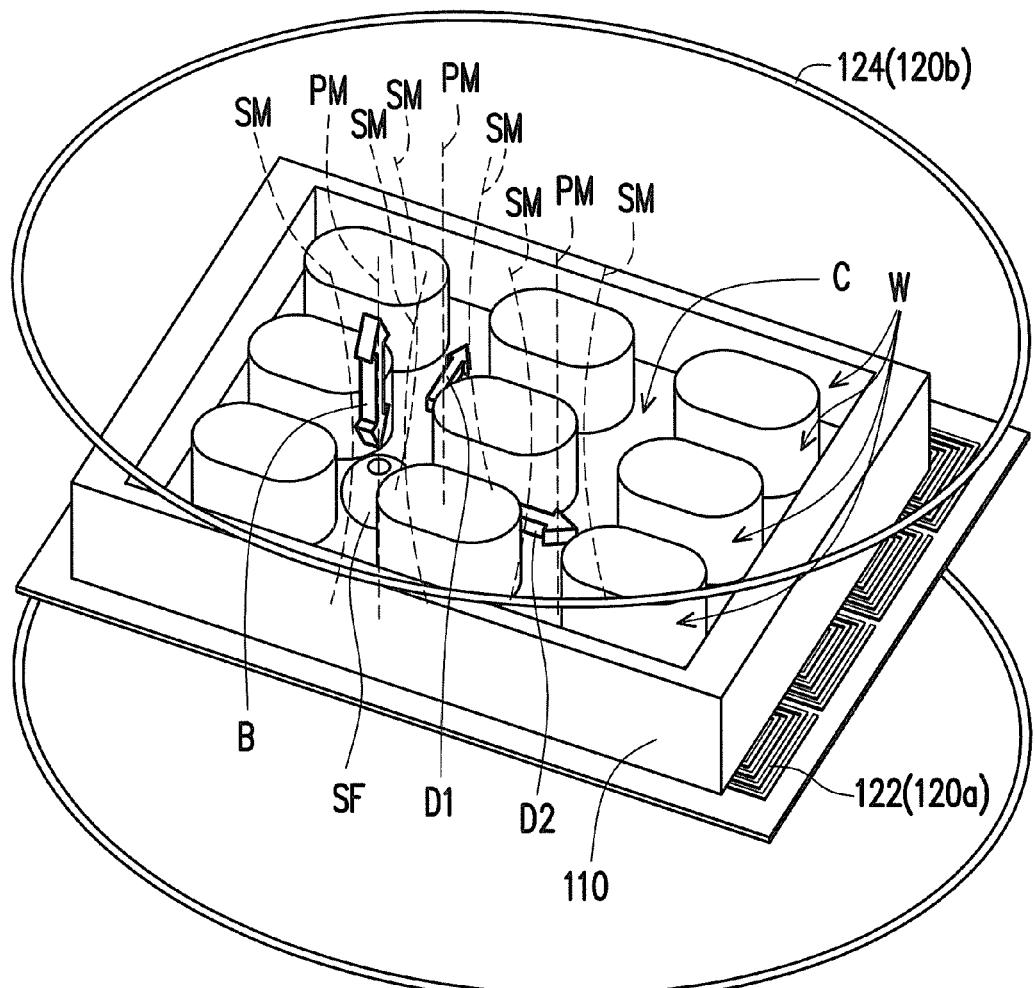
FIG. 5 is a schematic diagram of an apparatus for microfluid detection according to another embodiment of the disclosure.

FIG. 5 is a schematic diagram of an apparatus for microfluid detection according to another embodiment of the disclosure. Referring to FIG. 1A and FIG. 5, the apparatus for microfluid detection 500 of the present embodiment is similar to the apparatus for microfluid detection 100 in the embodiment of FIG. 1A, through in the present embodiment, the apparatus for microfluid detection 500 may have an array formed by the chambers C of a plurality of zones for examination ZE and a plurality of operational zones Z and the microfluidic channels 114 between the chambers C. Correspondingly, the ring-shape hollow magnetic generating module 120a can be an array formed by a plurality of magnetic generating coils. In this way, the apparatus for microfluid detection 500 may move the sample fluid SF on the same microfluidic chip 510 to different chambers C according to a actual requirement to implement a plurality of optical or non-optical detections (for example, the sample fluid SF in FIG. 5 can be moved to different chambers C along a direction D1 or a direction D2, though the disclosure is not limited thereto), and movement and positioning of the sample fluid SF between the zones for examination and the operational zones Z, and changing of the distribution of the magnetic particles can also be controlled by the magnetic fields as that described in the embodiment of FIG. 1A. In this way, by using the integrated apparatus for microfluid detection 500, effects of reducing signal interference, improving detection efficiency and increasing detection items can be achieved in case that a very small amount of samples is applied.

In summary, the apparatus for microfluid detection of the disclosure may controls to move the sample fluid carrying the magnetic particles to the zone for examination by using the positioning magnetic field, and may use the surrounding magnetic field to spread the magnetic particles in the sample fluid to the periphery region, such that none magnetic micro-particle exists in the transmission path of the detection beam. In this way, not only movement and positioning of the sample fluid can be effectively controlled, influence of the magnetic particles on the optical detection can be reduced to the minimum. Moreover, the operational zone has the hydrophobicity, and the zone for examination has the hydrophilicity, which avails movement of the sample fluid in the operational region and positioning of the same in the zone for examination. Moreover, the operational zone and the zone for examination can be a plurality of chambers formed by the side walls, and a distance between the side walls at two sides of the operational zone and the zone for examination is approximately the same to a length of the sample fluid. Namely, the sample fluid in the chamber can be stably confined by the side walls, such that stableness of positioning is increased, and efficiency and accuracy of optical detection are enhanced.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An apparatus for microfluid detection, adapted to detect a sample fluid comprising a plurality of magnetic particles, the apparatus for microfluid detection comprising:
    a microfluidic chip, comprising a substrate and microfluidic channels formed on the substrate, wherein the sample fluid is carried by a carry surface of the substrate; and
    a magnetic generating module, comprising a ring-shape hollow magnetic generating module and a surrounding magnetic generating module, wherein the ring-shape hollow magnetic generating module is disposed on at least one side of the carry surface, and the ring-shape hollow magnetic generating module is adapted to provide a positioning magnetic field to the sample fluid, the surrounding magnetic generating module is disposed at periphery of the microfluidic chip, and the surrounding magnetic generating module is adapted to provide a surrounding magnetic field to the sample fluid,
    wherein the magnetic generating module controls to move the sample fluid and change a distribution of the magnetic particles in the sample fluid through the positioning magnetic field and the surrounding magnetic field.

2. The apparatus for microfluid detection as claimed in claim 1, wherein during the detection, the surrounding magnetic generating module provides the surrounding magnetic field to the sample fluid, and the surrounding magnetic field drives the magnetic particles in the sample fluid to present a plurality of columnar stacking patterns in the sample fluid.

3. The apparatus for microfluid detection as claimed in claim 2, wherein the surrounding magnetic generating module comprises surrounding magnetic generating coils disposed on at least one of an upper side and a lower side of a zone for examination of the microfluidic chip, and the surrounding magnetic field is generated by the surrounding magnetic generating module.

4. The apparatus for microfluid detection as claimed in claim 3, wherein the surrounding magnetic generating coils are disposed on at least one of the upper side and the lower side of the zone for examination of the microfluidic chip.

5. The apparatus for microfluid detection as claimed in claim 1, wherein during operation, the ring-shape hollow magnetic generating module provides the positioning magnetic field to the sample fluid, and the positioning magnetic field drives the sample fluid to move from the operational zone of the substrate to the zone for examination of the substrate through the microfluidic channel for positioning.

6. The apparatus for microfluid detection as claimed in claim 5, wherein the ring-shape hollow magnetic generating module comprises a plurality of positioning magnetic generating coils disposed and arranged at the lower side of the microfluidic chip, and the positioning magnetic field is generated by the positioning magnetic generating coils.

7. The apparatus for microfluid detection as claimed in claim 5, wherein the ring-shape hollow magnetic generating module comprises a plurality of positioning magnetic generating coils disposed and arranged at the upper side of the microfluidic chip, and the positioning magnetic field is generated by the positioning magnetic generating coils.

8. The apparatus for microfluid detection as claimed in claim 5, wherein the operational zone has a hydrophobicity.

9. The apparatus for microfluid detection as claimed in claim 5, wherein the zone for examination has a hydrophilicity.

10. The apparatus for microfluid detection as claimed in claim 5, wherein the microfluidic chip comprises side walls at least located to both sides of the microfluidic channel, and the operational zone and the zone for examination are chambers formed by the side walls, wherein the microfluidic channel is a slit between the chambers, and sizes of the operational zone and the zone for examination are greater than a size of the microfluidic channel.

11. The apparatus for microfluid detection as claimed in claim 10, wherein a distance between the side walls at two sides of the operational zone and the zone for examination is approximately the same to a length of the sample fluid.

12. The apparatus for microfluid detection as claimed in claim 1, further comprising:
    an optical detection module, disposed on at least one side of the carry surface and comprising a light source and a detector, wherein during the detection, the light source provides a detection beam to the sample fluid, the ring-shape hollow magnetic generating module and the surrounding magnetic generating module drive the magnetic particles to spread, so as to form a central zone without the magnetic particles in the sample fluid, and the detection beam passes through the central zone and is transmitted to the detector.

13. The apparatus for microfluid detection as claimed in claim 12, wherein the light source and the detector are respectively disposed at different sides of the microfluidic chip relative to the carry surface, the microfluidic chip is light transparent, and the detection beam passes through the sample fluid and the microfluidic chip and is transmitted to the detector.

14. The apparatus for microfluid detection as claimed in claim 12, wherein the light source and the detector are located at a same side of the microfluidic chip and located at the same side with that of the carry surface, the microfluidic chip is light reflective, and the detection beam passes through the sample fluid, and is reflected by the microfluidic chip, and is transmitted to the detector.

15. The apparatus for microfluid detection as claimed in claim 1, further comprising:
    an optical detection module, disposed on at least one side of the carry surface and comprising a light source and a detector, wherein during the detection, the light source provides a detection beam to the sample fluid, the ring-shape hollow magnetic generating module and the surrounding magnetic generating module drive the magnetic particles to gather, such that the magnetic particles are concentrated in a central zone of the sample fluid, and the detection beam passes through the central zone and is transmitted to the detector.

16. The apparatus for microfluid detection as claimed in claim 1, further comprising:

a thermal-modulation module, disposed on at least one side of the carry surface, and selectively increasing or decreasing a temperature of the sample fluid.

17. The apparatus for microfluid detection as claimed in claim 16, wherein the thermal-modulation module comprises a laser heater, and the laser heater heats the sample fluid.

* * * * *